(12) United States Patent
Bone et al.

(10) Patent No.: US 7,441,896 B2
(45) Date of Patent: Oct. 28, 2008

(54) MACULAR PIGMENT MEASUREMENTS

(75) Inventors: Richard Andrew Bone, Miami, FL (US); John Thomas Landrum, Miami, FL (US)

(73) Assignee: Millennium Diet and Neutriceuticals Limited, Cambridge (GB)

( * ) Notice: Subject to any disclaimer, the term of this patent is extended or adjusted under 35 U.S.C. 154(b) by 538 days.

(21) Appl. No.: 10/837,720

(22) Filed: May 3, 2004

(65) Prior Publication Data
US 2005/0010115 A1    Jan. 13, 2005

(30) Foreign Application Priority Data
May 1, 2003     (GB)  ................ 0310040.1
Dec. 29, 2003   (GB)  ................ 0330094.4

(51) Int. Cl.
*A61B 3/10* (2006.01)
(52) U.S. Cl. .............. 351/213; 351/206; 351/233; 351/246
(58) Field of Classification Search .......... 351/213
See application file for complete search history.

(56) References Cited

U.S. PATENT DOCUMENTS

| | | | |
|---|---|---|---|
| 4,922,919 A | 5/1990 | Novack | |
| 5,873,831 A | 2/1999 | Bernstein | |
| 6,315,412 B1 * | 11/2001 | Snodderly et al. | 351/200 |
| 6,329,432 B2 * | 12/2001 | Howard et al. | 514/725 |
| 6,556,853 B1 | 4/2003 | Cabib | |
| 6,578,965 B2 * | 6/2003 | Grant | 351/214 |
| 2002/0193948 A1 * | 12/2002 | Schweitzer et al. | 702/19 |

FOREIGN PATENT DOCUMENTS

| | | |
|---|---|---|
| EP | 0284248 A1 | 9/1988 |
| GB | 2378600 A | 2/2003 |
| WO | WO-98/25648 A3 | 6/1998 |
| WO | WO-99/29229 A1 | 6/1999 |
| WO | WO-00/06735 A1 | 2/2000 |
| WO | WO-02/080759 A2 | 10/2002 |

* cited by examiner

*Primary Examiner*—Jessica T Stultz
(74) *Attorney, Agent, or Firm*—Barnes & Thornburg LLP

(57) ABSTRACT

Apparatus for use in measuring the density and spatial distribution of macular pigment in an eye comprises a camera (4) for capturing a color image of an eye, at least one filter (36) for filtering light reaching the camera (preferably by filtering the light illuminating the eye). The filter (36) has a transmission spectrum with one peak in the region of light absorbed by the pigment and another peak in a region where no such absorption occurs. The filter increases the sensitivity of the camera to macular pigment while enabling the effect of other pigments to be reduced or eliminated. A method of measuring macular pigment involves obtaining a color image of an eye, the image having two color components each having a spectrum having a respective one of said peaks. Corresponding portions of the components are mathematically combined so as to provide a measurement of macular pigment density and the results of the combination are used to provide an output representative of the contribution of macular pigment to the image.

15 Claims, 6 Drawing Sheets

56

MACULAR PIGMENT MEASUREMENTS

FIELD OF THE INVENTION

This invention relates to apparatus for use in inspecting the density and spatial distribution of macular pigment in an eye, and to a method of determining said density and spatial distribution.

BACKGROUND TO THE INVENTION

Macular pigment is a yellow pigment situated in the central portion of the human retina. The absorption spectrum for the pigment has a peak for light of a wavelength of 460 nm and zero for light for a wavelength of 540 nm, so that the pigment absorbs significant amounts of the shorter wavelength light, whilst having little or no effect on light of the longer wavelength.

The highest concentrations of macular pigments are to be found in the region of the retina which has a very high number density of cone receptors, and is coupled with a disproportionately large area of the visual cortex, giving that region a high degree of visual acuity.

It has been proposed that the macular pigment protects the retina against harmful effects of short wavelength radiation, and accordingly much work has been devoted to measuring the optical density, and spatial distribution, of macular pigment in various subjects in order to determine whether there is any correlation between irregularities in the amount of macular pigment present and certain defects.

A flicker photometer is an instrument that enables a subjective measurement of macular pigment density to be made. The flicker photometer projects green and blue light in an alternating sequence into a subject's eye, and the subject is able to vary the relative intensity of light of one of those colours until a minimum or no flickering is perceived.

Photographic methods have also been used to obtain an objective indication of the macular pigment density/spatial distribution, but in order to be effective, have involved dilating the subjects pupil, bleaching photo pigments to minimise their contributions and then photographing the fundus twice, once in blue light and once in green light. Those images are then digitised (if not already captured by a CCD camera), combined in registration with each other, logarithmically transformed and then subtracted.

However, ensuring that the images are precisely registered, is a time consuming step which places high demands on image processing software and hardware.

SUMMARY OF THE INVENTION

According to a first aspect of the invention, there is provided apparatus for use in measuring the density and spatial distribution of macular pigment in an eye, the apparatus comprising a camera for capturing a colour image of the retina of an eye under examination, filter means for filtering light reaching camera, the filter means having a transmission spectrum which has a peak in the region of the wavelength of light absorbed by the pigment and another peak in a region at which no such absorption occurs.

A conventional colour camera can obtain a colour image from a single exposure, but this image, whilst providing a representation of the colour of the photographed features, does not have sufficient colour resolution for use in the measurements of macular pigment density/spatial distribution. However, the filter of the present invention increases the sensitivity of the apparatus to said macular pigment since the filter will pass light having a component at the peak of absorption of the macular pigment and another which will be unaffected by the pigment, so that the captured image has a component which is greatly affected by macular pigment density and another, reference component which is not.

Since both components are present in a single image, there is no need for separate images to be obtained, and the invention therefore also avoids the problem of achieving image alignment. In addition, a conventional camera can be used, so that apparatus in accordance with the invention may be relatively cheap to produce.

In order to provide good resolution, the filter means preferably has a transmission spectrum which is substantially zero between said two peaks. To that end the transmission spectrum may to advantage not exceed 0.001% between said peaks. Preferably each peak is no more than 40 nm wide.

The filter means may be placed anywhere in the path of light which illuminates the eye and travels to an image capture device, for example one or more CCD arrays in the camera. Preferably, however, the filter means is situated in between the eye and an illuminating light source, so that the spectrum of light which illuminates the eye has said peaks. Thus, for example, a conventional 3 CCD array retinal camera, which typically has a flash lamp and an associated and interchangeable filter for the flash lamp, can be converted into apparatus according to the invention, simply by replacing the existing filters with said filter means.

Since the advantages of the invention can be achieved by selecting an appropriate spectrum of illuminating light, there is provided, in accordance with the second aspect of the invention, apparatus for use in the measuring of the density and spatial distribution of macular pigment in an eye under examination, the apparatus comprising illumination means for illuminating said eye and a camera for capturing a colour image of the eye, when so illuminated, wherein the illumination means is operable to illuminate the eye with light the spectrum of which has a first peak at a wavelength of light which is absorbed by the macular pigment and a second peak at a wavelength at which substantially no such absorption occurs.

Preferably, the spectrum of said illuminating light falls to substantially zero between these two peaks.

The filter means preferably comprises a single filter having both said peaks in its transmission spectrum.

Preferably, one of said peaks is at the wavelength corresponding to blue light, the other at that corresponding to red light.

Preferably, said first peak is at 460 nm, the second at 600 nm.

The filter may conveniently be a triple bandpass filter, the transmission spectrum of which has a further peak and a wavelength corresponding to green light (e.g. 540 nm).

The filter may be a proprietary item available from, for example, OMEGA OPTICAL.

Preferably, the apparatus includes an image processor for processing the image captured by the camera, wherein the image processor is programmed to subtract the reference component of the image from the component in the absorption spectrum of the macular pigment, thereby to remove the contribution to the image of pigments other than the macular pigment.

Preferably, the processor is operable to display the results of the subtraction as a macular pigment map.

Preferably, said subtraction is of the logs of the intensities of the two components.

Preferably the image processor is operable to take the logs of three images, each corresponding to a respective peak of the triple bandpass filter's transmission spectrum, and to combine these so as to eliminate any contributions from non uniform distributions of both melanin and photopigments.

If, however, the haemoglobin and melanin are uniformly distributed in the retina, they will cause a uniform reduction in image intensity, which leaves only three unknown pigment distributions: macular pigment, rod photopigment and cone photopigment.

In this case, the image processor is preferably operable to determine, from the three images, the distributions macular pigment, rod photopigment and cone photopigment across the retina.

According to a third aspect of the invention, there is provided a method of measuring macular pigment density and spatial distribution in an eye, the method comprising the steps of, a) capturing a colour image of the retina of the eye, the image having a first and second colour component, the first colour component having a spectrum the peak of which is at a wavelength at which the absorption by macular pigment is at a maximum and a second peak at which substantially no such absorption occurs;

b) subtracting one of the image components from the other, at each region of the image, to remove at least some colour contributions not arising from the macular pigment and c) providing an output representative of the contribution of the macular pigment to the image.

Preferably the step of capturing the image involves illuminating the eye with light, the spectrum of which has said first and second peaks.

The image may be captured by means of a camera and a filter which has a first and second peak its transmission spectrum, corresponding to the two peaks of the components, and which filters the light forming the image captured by the camera. The filter may be in the path of light from the eye under examination to the camera, but is preferably in the path of light from a source of illumination to the eye.

BRIEF DESCRIPTION OF DRAWINGS

The invention will now be described, by way of example only, with reference to the accompanying drawings in which.

DETAILED DESCRIPTION

Figure 1:
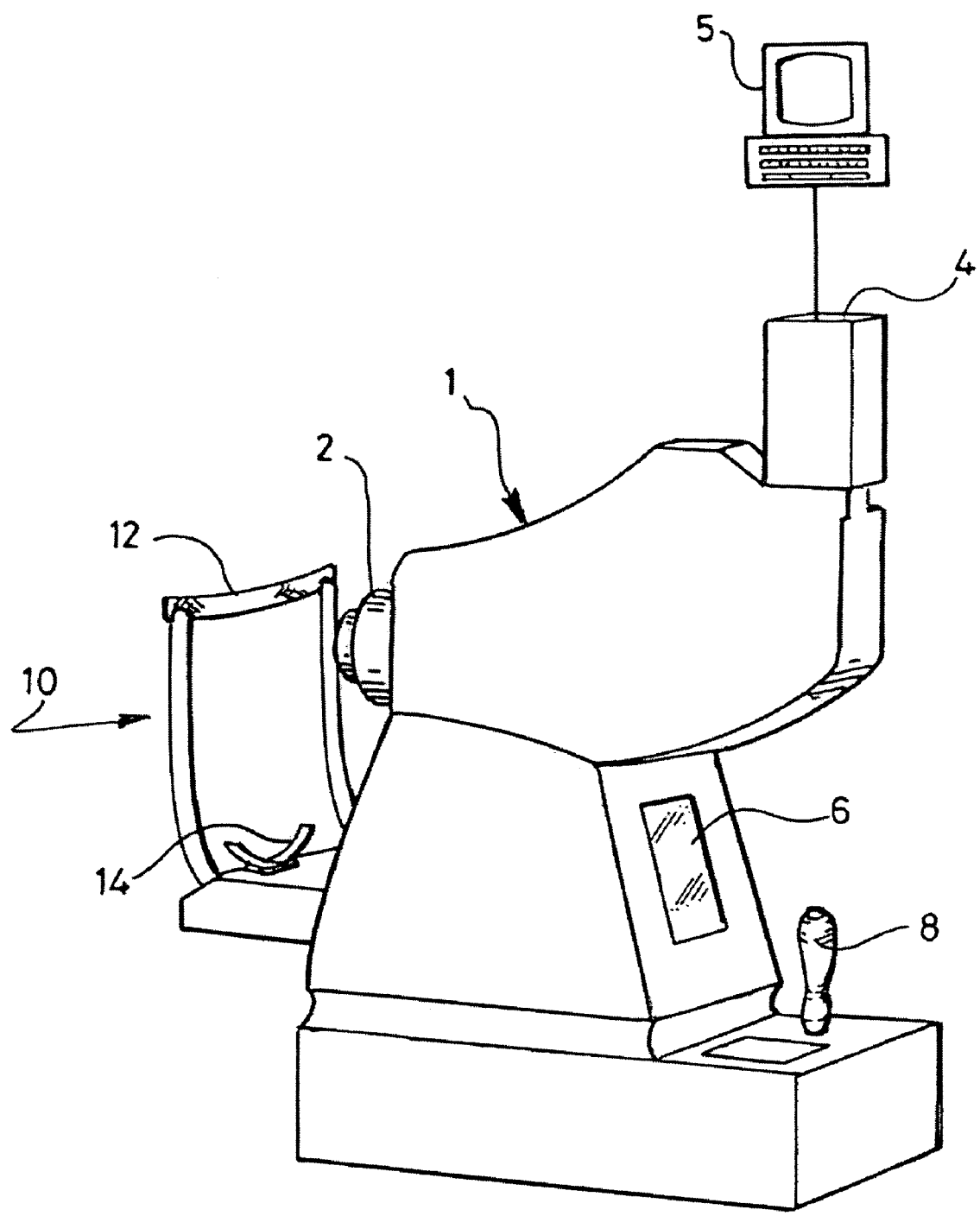
FIG. 1 is an external view of apparatus in accordance with the invention.

The camera shown in FIG. 1 is a modified version of a non mydriatric retinal camera, in this case the TOPCON TRC-NW6SF camera. The camera comprises a housing 1 containing illumination and imaging optics and a flash lamp. At one end of the housing 1 there is an objective lens assembly 2, and at the other end a 3CCD (charge coupled device) camera 4 for generating a three component colour output signal representative of a captured image obtained via the imaging optics in the housing 1. The rear of the housing 1 is also provided with an LCD view finder screen 6, and supports a shutter control 8. Attached to the front of the housing 1 is a head support 10 comprising a headband 12 and a chin rest 14. The head support 10 locates the head of the subject to facilitate the correct positioning of the eye under examination relative to the objective lens assembly 2.

Figure 2:
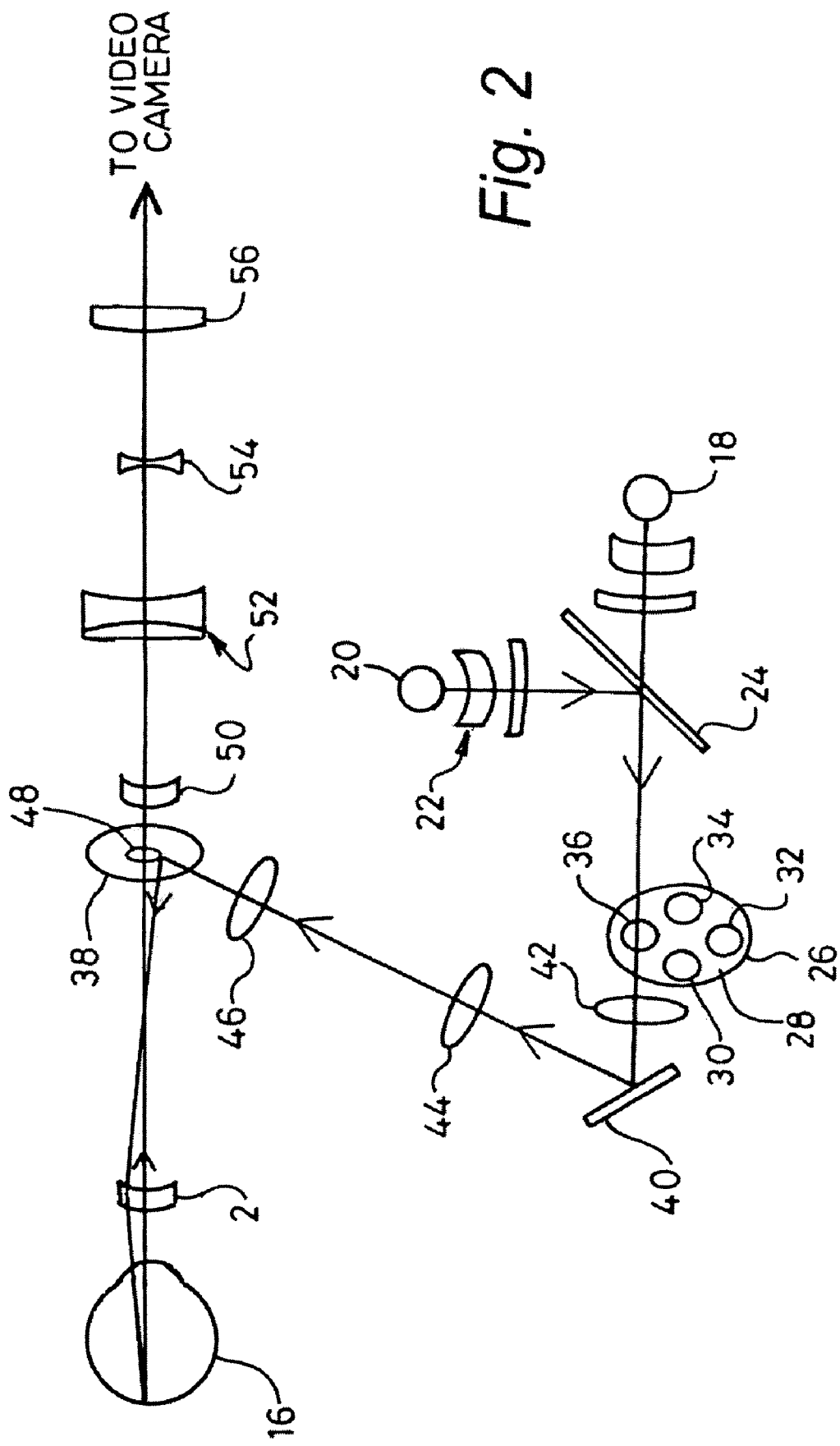
FIG. 2 is a simplified schematic view of optical elements and paths within the apparatus.

FIG. 2 shows, in simplified form, the illumination and imaging optics within the housing 1, as well as an eye under examination 16, the camera's flash lamp 18 and a focusing lamp 20. The focusing lamp 20 is used to illuminate the eye 16 while the operator is setting up the camera to photograph that eye. The illumination provided by the lamp 20 enables the image of the retina of eye 16 to be viewed on the view finder screen 6 so that the operator can correctly position the eye and focus the camera. Light from the lamp 20 passes through a focusing lens system 22 to a beam splitter 24 in the form of a half silvered mirror, from which it is reflected through a filter assembly 26. The assembly 26 comprises a holder 28 which holds four filters, respectively referenced 30, 32, 34, and 36, and which is rotatable about an axis parallel to the beam of light from the focusing lamp 20 to bring any selected one of those filters into registry with that beam. It will be appreciated that a holder capable of carrying different numbers (more or fewer) filters could be used in the camera. In the present case, the filters 30-34 are used for standard retina photography, whilst the filter 36 is a triple bandpass filter, described below, which enables the image captured by the camera to be used to measure macular pigment density and spatial distribution on the retina of the eye 16.

Light passing through the filter 36 then passes to an annular mirror 38 via a reflecting mirror 40 and focusing lenses 42, 44 and 46. The mirror 38 reflects that light via the objective lens assembly 2 into the eye 16 to illuminate the retina of that eye. That light is reflected from the retina and some of it passes back through the lens 2 which directs the light through the aperture (referenced 48) in the mirror 38, through a further system of lenses 50, 52, 54 and 56 which focus an image of the illuminated retina onto the image plane of the CCD camera 4. The TOPCON TRC-NW6 camera is supplied with a neutral filter for use in normal colour photography (for example for use in diabetic screening) and an exciter filter for use in fluorescein angiography. These filters may be interchanged with other filters, and modification to the camera necessary to convert it into apparatus according to the invention is achieved by replacing one of those filters with the triple bandpass filter 36. In reality, the camera has a more complex arrangement of optical elements than is indicated by FIG. 2, but since these are, save for the filter 36, identical to those used in the known camera, they have not been described in detail.

The output of the camera 4 is connected to a computer 5 which has a video capture card for enabling the output to be recorded onto the computer's hard drive for subsequent processing.

The CCD camera 4 has three CCD arrays and associated red, green and blue colour filters. Each CCD array is positioned behind a respective one of the three filters, and the camera includes a beam splitter for projecting the image of the retina of the eye 16 onto each of the 3 CCD arrays through its respective filter. The output of each array will therefore represent an array of grey scale pixel values which itself constitutes an intensity map of the filtered light received from the retina. The output of the CCD arrays therefore constitutes red, green and blue channels.

Figure 8:
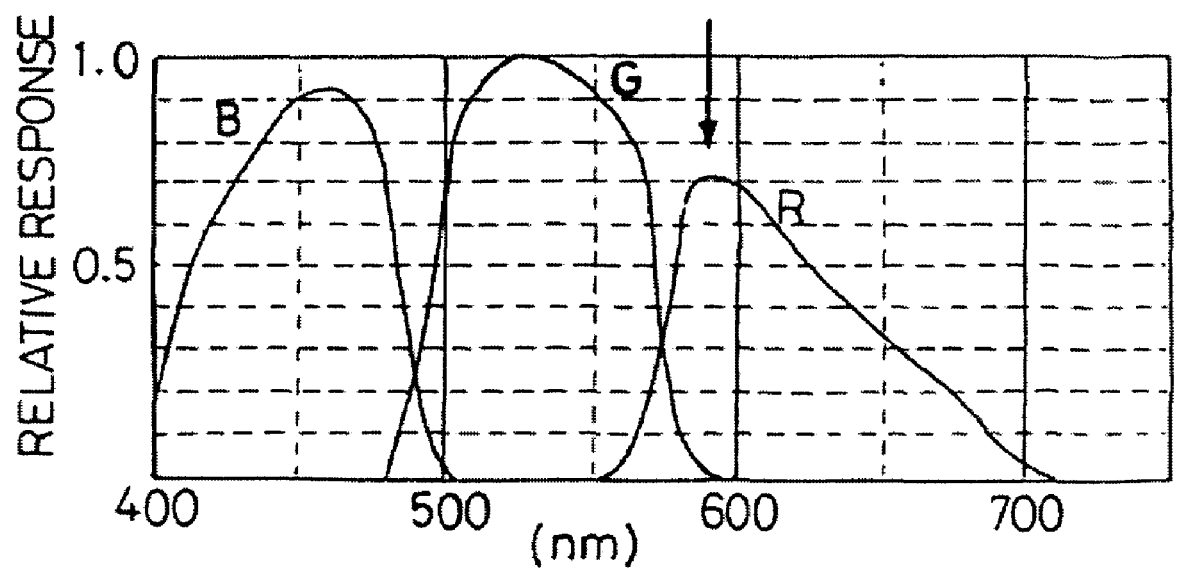
FIG. 8 shows a spectral response from 3 CCDs used by the apparatus to provide an electrical output signal representative of a captured image of a retina.

FIG. 8 illustrates the spectral response of the blue (B) green (G) and red (R) channels in the camera 4. Were white light to be used to illuminate the retina under inspection, the blue green and red channels of the camera output would not provide sufficient colour resolution to enable macular pigment density to be measured. However, the spectral responses from the three CCD arrays in the camera 4 will be shaped into narrower wave bands by the filter 36, since the transmission spectrum of this filter has three relatively narrow bands, referenced 50, 52 and 54 in FIG. 3, in its transmission spectrum. The width of each of these bands is considerably narrower than that of the three bands, B, G and R, the transmission spectrum between adjacent bands is substantially zero, as is illustrated in the optical density map of FIG. 4 in which the vertical axis is minus one multiplied by the log (to base ten) of the transmittance. Thus, the transmittance of the triple band-pass filter 36 between the transmission bands does not exceed 0.00001 (i.e an optical density of 5). A filter having these spectral characteristics is available from Omega Optical. The interaction between the triple bandpass filter 36 and the filters in the CCD camera 4 is such that, of the light transmitted through the filter 36, the light within the band 50 will only affect the blue output channel for the camera 4, all light in the band 52 will affect the green channel whilst light in the band 54 only appears in the red channel. Thus, light transmitted in each of the three bands of the bandpass filter 36 will only affect the output from a respective one of the 3 CCD arrays in the camera 4.

The method of operation of the apparatus, and the analysis of the retinal image captured by the apparatus, will now be described.

Initially, the subject places his or her head against the head support 10, and the focusing lamp 20 and camera 4 are activated respectively to illuminate the eye 16 and to. capture a video image thereof. That image is displayed on the display 6 and the operator adjusts the controls of the camera to focus and align that image. The manner of this adjustment is the same as for the known retinal camera on which the present apparatus is based.

Figure 3:
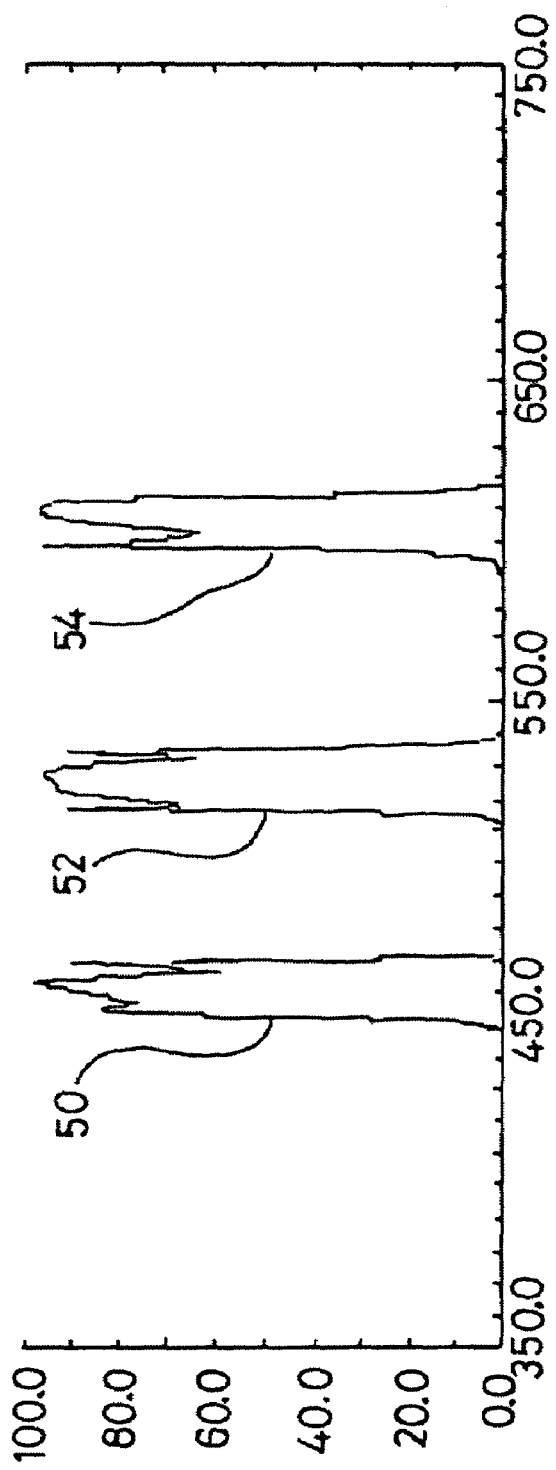
FIG. 3 is the transmission spectrum of a triple bandpass filter used in the apparatus.
Figure 4:
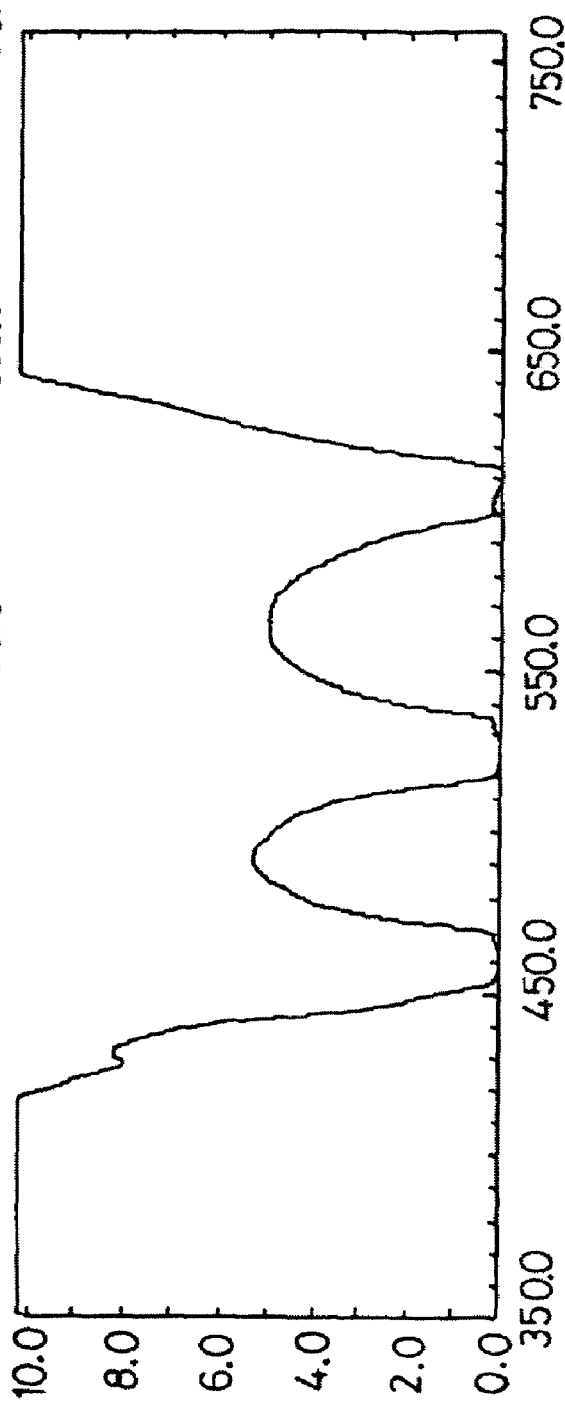
FIG. 4 is the optical density plot for the triple bandpass filter.

The operator then activates the shutter switch, causing the lamp 18 to flash and a shutter (not shown) in the camera 4 to operate, so that the camera 4 captures the colour image of the retina of the eye 16 when the latter is being illuminated by the lamp 18 through the filter 36, i.e. with light having a spectrum corresponding to the transmission spectrum of FIG. 3.

The camera supplies R, G and B signals to the computer 5, said signals representing an array of grey scale pixel values for each of the 3 CCD arrays.

Image analysis software (for example Imagepro Plus) which has been pre-installed on the computer 5 is then used to analyse the captured image. This is a powerful application capable of performing many operations, including those needed to generate an optical density map of the macular pigment of the retina. However, it is envisaged that other, simpler software packages could be used to achieve the same end, using an analysis technique developed from the underlying theory summarised below.

We will assume a general situation of non-uniform illumination of the retina by the camera's flash lamp. Let the incident intensities by $I_{F,B}$, $I_{F,R}$, $I_{P,B}$ and $I_{P,R}$, where the subscripts F and P refer to a foveal and peripheral retinal location (no macular pigment), and the additional subscripts B and R refer to the blue (460 nm) and red wavelength bands, respectively of the light source (i.e flash lamp 18 and filter 36). The analysis would not be affected if the green wavelength band had been chosen instead of the red. Similarly let $R_{F,B}$, $R_{F,R}$, $R_{P,B}$ and $R_{P,R}$ be the corresponding reflectances of all retinal layers posterior to the macular pigment. Finally, T is the 460 nm transmittance of the macular pigment at the foveal location, and the logarithms/log differences in this description are to base ten.

For the blue illumination, the log difference in reflected intensities between the foveal and peripheral locations will be given by $$LD_B = \log I_{F,B}T^2 R_{F,B} - \log I_{P,B}R_{P,B} = \log\frac{I_{F,B}T^2 R_{F,B}}{I_{P,B}R_{P,B}},$$

and for red illumination by $$LD_R = \log I_{F,R}R_{F,R} - \log I_{P,R}R_{P,R} = \log\frac{I_{F,R}R_{F,R}}{I_{P,R}R_{P,R}}$$

The factor $T^2$ in the first equation is due to the double passage of the light through the macular pigment.

Subtracting, (1)

$$LD_R - LD_B = \log\frac{I_{F,R}R_{F,R}I_{P,B}R_{P,B}}{I_{P,R}R_{P,R}I_{F,B}T^2 R_{F,B}}$$

The spectral distributions of light on the fovea and periphery will be the same, $$\therefore \frac{I_{F,R}}{I_{F,B}} = \frac{I_{P,R}}{I_{P,B}}.$$

It will also be assumed that the reflectance spectrum is the same in each location, $$\therefore \frac{R_{F,R}}{R_{F,B}} = \frac{R_{P,R}}{R_{P,B}}$$

Equation (1) then becomes $$LD_R - LD_B = \log\frac{1}{T^2} = 2D$$

where D (=−log T) is the optical density of the macular pigment at 460 nm. Thus $$D = \tfrac{1}{2}(LD_R - LD_B) \qquad (2)$$

Using ImagePro Plus, the spatial distribution of D is obtained from a single retinal image as follows:

1. Individual grayscale images are extracted from the original image, corresponding to the modified blue and red (and green) channels of the camera 4.

2. The greyscale images are transformed to floating point format to minimise loss of information in the subsequent steps.

3. The "red" and "blue" images are logarithmically transformed.
4. The "log blue" image is subtracted from the "log red" image.
5. The resulting image is halved, in accordance with equation (2).

Figure 5:
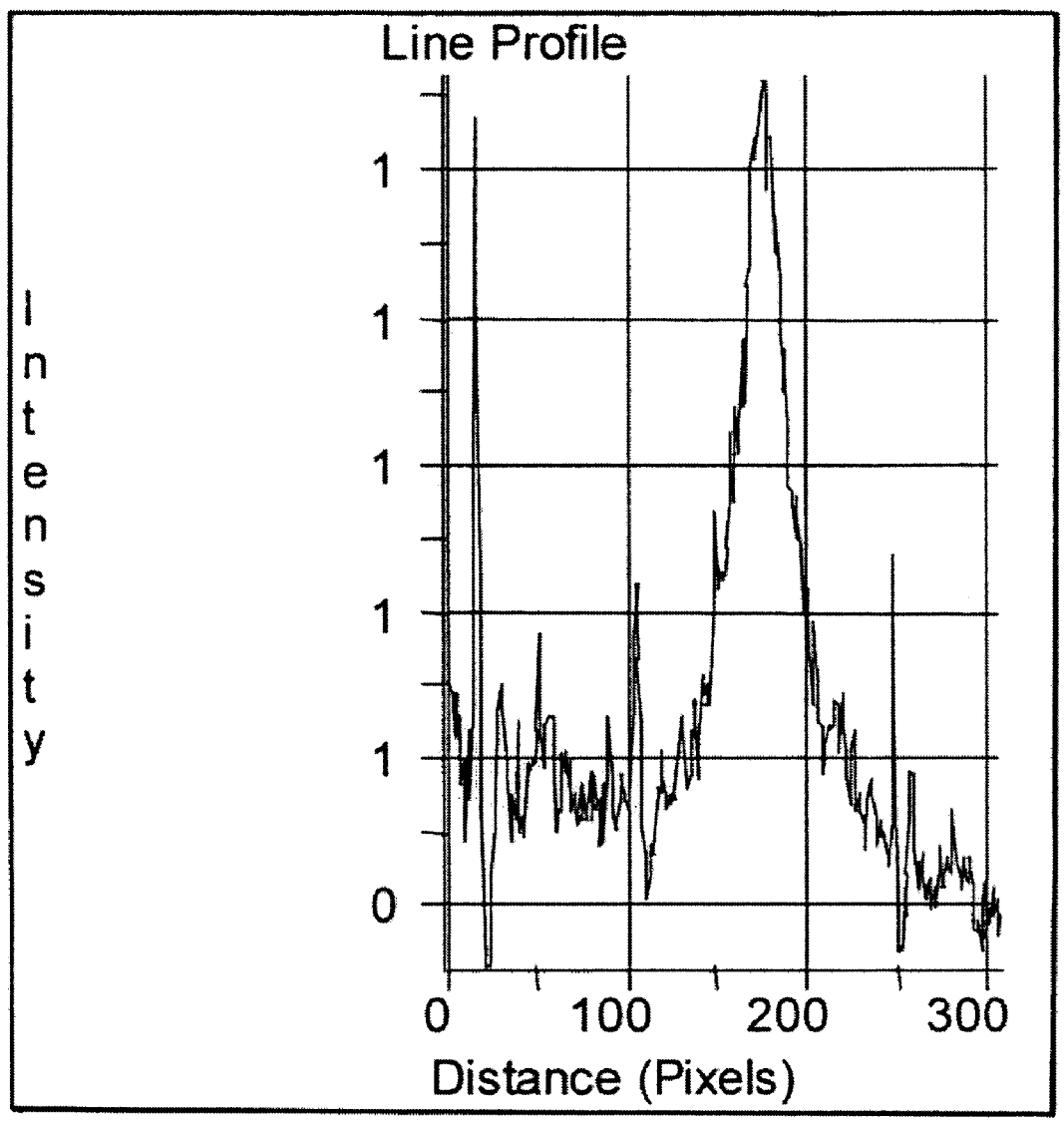
FIG. 5 is a plot of calculated macular pigment density against position along a vertical line passing through the fovea in the retina of an eye under examination.
Figure 6:
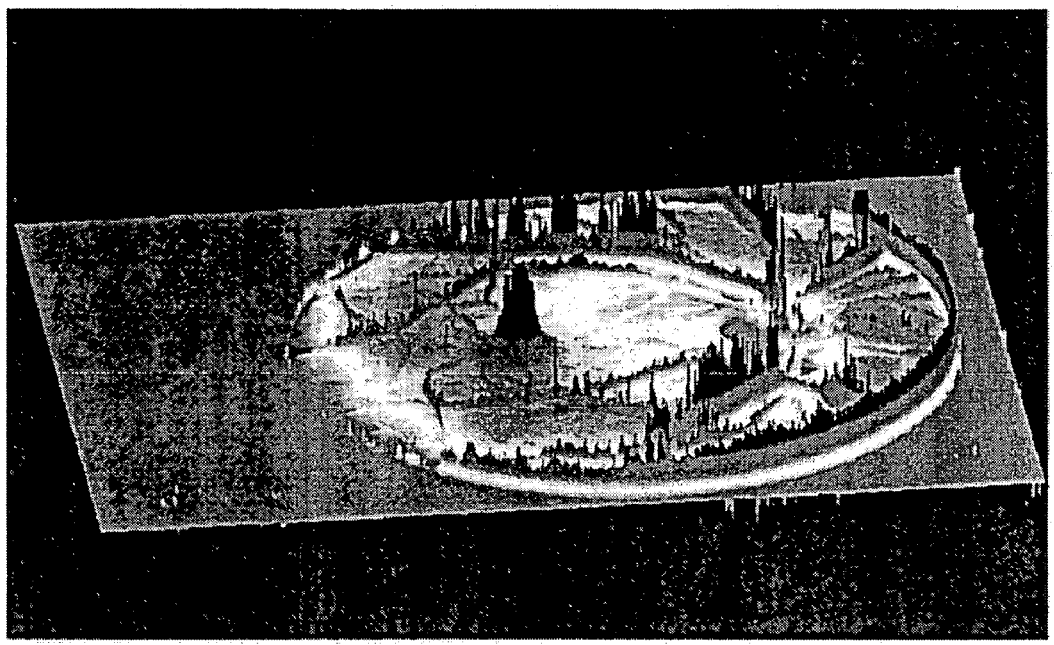
FIG. 6 is a surface plot showing calculated macular pigment density across a retina.
Figure 7:
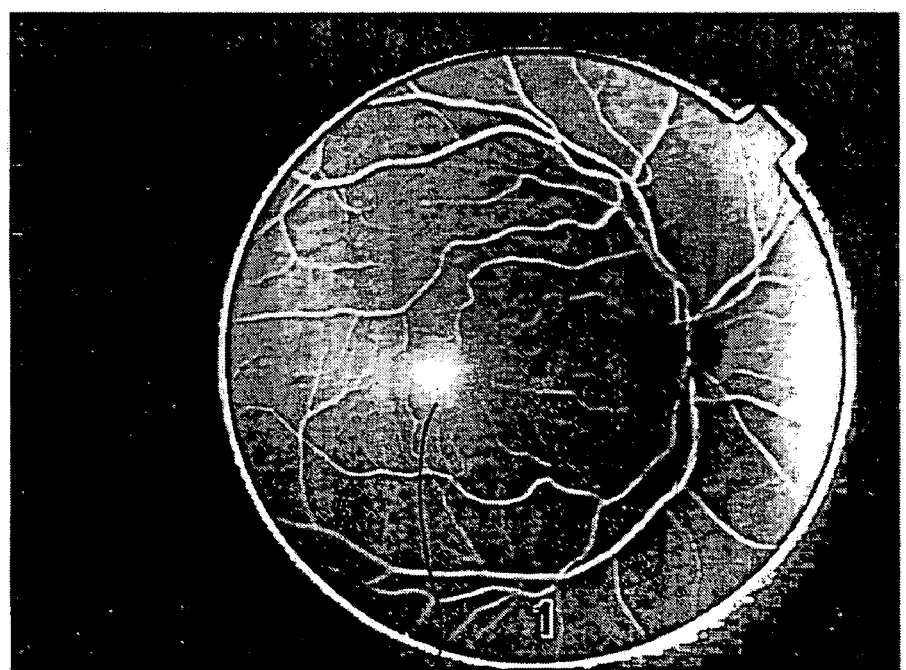
FIG. 7 is an image of a retina photographed using apparatus according to the invention.

The result will be a grayscale image, an example of which is shown in FIG. 7, in which the light area 56 is the area of macular pigment. A variety of options is available for further analysis or presentation. The image may be rendered as a surface plot as in FIG. 6 in which the area of macular pigment is shown as a "hill" in the centre of the image. A density scan may be made along a line through the fovea, for example along horizontal or vertical meridians. An example is shown in FIG. 5. From such a plot, the peak macular pigment optical density will be obtained as the difference between the pixel values at the peak and at a peripheral location, such as 8° above the fovea. Alternatively, a circular "area of interest" corresponding to, say, 1.5° may be defined. The average pixel value along the circular line, or the average pixel value within the enclosed area, may be obtained. There is evidence that flicker photometry determines the macular pigment density at the edge of the stimulus rather than the average value over the stimulus area. Thus, if a comparison is to be made between flicker photometry and reflectometry, determining the average pixel value along the circular line may be more appropriate.

The new method offers several advantages over traditional reflectometry, which requires the acquisition of separate blue and green images that must be precisely registered with each other. Such alignment is possible with ImagePro, but it would be too time-consuming for large-scale screening. With the proposed procedure, the blue and red images will be extracted from a single image and will be perfectly registered. Also, when separate images are acquired, there is the problem of non-uniform illumination of the retina that may be different in the two images. As can be seen in the derivation of equation (2), any non-uniformity is the same in both images, if these are extracted from a single image, and is self-cancelling.

There remains the question of whether to use a red or green image as the reference image. Either fulfils the requirement of showing zero or near zero macular pigment optical density. However, the green image shows a darkening in the same region as the macular pigment due to the presence of long and medium wavelength cone photopigments. To minimise the contribution of these photopigments, they would normally have to be bleached (approx. 5.6 log Td for approx. 3 minutes) prior to the acquisition of the image. However, with a method in accordance with the invention a triple bandpass filter 36 with the red transmitting band centred at approx. 600 nm is used. At this wavelength, the optical density of the cone photopigments is approximately the same as at 460 nm, the centre of the blue transmitting band. This photopigment optical density will contribute equally to the red and blue images and will be eliminated by the subtraction process. At 600 nm, rod photopigment optical density is approx. zero, but this is not the case at 460 nm and could affect the comparison between the foveal and peripheral sites in the blue image. However, the optical density at 500 nm has been estimated to be about 0.016 at 7° to 10° from the fovea (Brindley G. S. and Willmer E. N.(1952). The reflexion of light from the macular and peripheral fundus oculi in man. J. Physiol. 116, 350-356). This would correspond to roughly 0.01 at 460 nm and is comparable with the estimate of "Delori F. C., Goger D. G., Hammond B. R., Snoddlerly D. M., Burns S. A. (2001) Macular pigment density measured by autofluorescence spectrometry: comparison with reflectometry and heterochromatic flicker photometry. J. Opt. Soc. Am., A, Optics, Image Science, & Vision 18, 1212-30. Assuming no rods at the foveal site, macular pigment optical density would be underestimated by only about 2 to 4% in the average subject.

Apart from photopigments, melanin and oxyhaemoglobin can potentially influence macular pigment measurements obtained by reflectometry. Oxyhaemoglobin can probably be ignored because its density is the same in the fovea and periphery (12°). Melanin may pose a problem since it has been shown to have a non-uniform distribution in the retina, peaking in the macula. Also it has an absorbance spectrum that decreases with increasing wavelength. Thus the blue image would be the most affected, the green image would be moderately affected, and the red image would be least affected. This would tend to cause the macular pigment optical density to be overestimated by a factor that would be larger if the red image is used as the reference rather than the green. In principle, the effects of melanin can be removed. To achieve this, theory indicated that equation (2) would need to be replaced by $$D = 1/2(rLD_R - LD_B) \qquad (3)$$

where r is the ratio of the melanin extinction coefficients at 460 and 600 nm (approx. 4). Hence the "log red" image would need to be multiplied by r prior to subtracting the "log blue" image. However, it should be noted that equation (3) assumes uniform illumination of the retina and a spectrally flat reflector. In addition, the value D given by (3) will be affected by any non-uniform distribution of photopigment across the retina. By exploiting the green image, as well as the blue and red images, we can eliminate the contributions from non-uniform distributions of both melanin and photopigments. The appropriate equation for D is then $$D = 1/2\left[LD_R \frac{r_2 r_4 (r_1 - r_3)}{r_1 r_4 - r_2 r_3} - LD_B + LD_G \frac{r_1 r_3 (r_4 - r_2)}{r_1 r_4 - r_2 r_3}\right] \qquad (4)$$

where the coefficients, $r_n$, are the ratios of melanin or photopigment extinction coefficients at different pairs of wavelengths. More specifically the r factors are as follows:

$r_1$=ext. coeff. at the blue wavelength/ext. coeff. at the green wavelength for melanin $r_2$=ext. coeff. at the blue wavelength/ext. coeff. at the red wavelength for melanin $r_3$=ext. coeff. at the blue wavelength/ext. coeff. at the green wavelength for cone photopigment $r_4$=ext. coeff. at the blue wavelength/ext. coeff. at the red wavelength for cone photopigment The ratios are obtainable from the literature. To put equation (4) into practice, the "log red", "log green" and "log blue" images will be linearly combined using the appropriate multipliers shown in the equation.

Here, D is the optical density of the macular pigment at the wavelength of the blue filter band (460 nm) and $LD_R$, etc are the logarithmically transformed red, green and blue grayscale images. The software (ImagePro Plus) is Windows-based and performs each of the following steps.

1. Individual grayscale images are extracted from the original image, corresponding to the filter-modified blue and red and green channels of the camera.
2. The "red" "green" and "blue" grayscale images are transformed to floating point format to minimise loss of information in the subsequent steps.

3. The three grayscale images are logarithmically transformed.
4. The 3 logarithmically transformed images are combined according to equation (4).

The result is an image of the retina that shows a lighter area (higher intensity/higher pixel value) in the region of the macula. A "value" of macular pigment density may be found by taking the average of a set of pixel values within a circular region (e.g. 1 degree in diameter) centred on the centre of the macula, and subtracting the average of a similar set centred at a reference location at, say, 8 degrees from the centre of the macula (where macular pigment density≈0). This would provide the average macular pigment density in the central 1 degree.

It will be appreciated that in the maps/plots of FIGS. 5-7, each individual pixel represents a mathematical combination of the amounts of light transmitted through each band of the triple bandpass filter, subsequently reflected from the retina, and modified in the central part of the retina by the transmitting properties of the macular pigment. Thus the macular pigment optical density, D at any point within this central part of the retina is obtained by subtracting from the corresponding pixel value the pixel value at some non-central retinal location, such as at an eccentricity of 8°, where macular pigment density is known to be negligible. For example, in FIG. 5, the peak optical density D is obtained by subtracting from the peak ordinate value the ordinate value at pixel number 95, this representing a point on the retina approximately 8° from the centre of the fovea.

Notwithstanding the above comments on the distribution of rod photopigments, it is believed that the effect of such pigments on the macular pigment measurement may be eliminated by using an image of the retina illuminated by light at a fourth wavelength. In order to obtain the second image, the triple bandpass filter 36 is exchanged for a filter with peak transmittance at 680 nm and a bandwidth of 20 nm and the eye under examination is photographed a second time. The first photographs yields the 'red' green' and 'blue' images, one from each respective CCD array, whilst the second photograph yields a second 'red' image (at a wavelength longer than that of the first 'red' image). There are therefore 4 images at difference wavelengths, and these can be used to obtain the macular pigment optical density in a way which eliminates the (small) effect of rod photopigment.

Here, briefly, is how we would obtain the macular pigment optical density distribution, including this new refinement:

1. Obtain an image using the triple bandpass filter. Use image analysis software to extract the grayscale images corresponding to the red, green and blue channels, as before, and concert these to logs ($LD_R, LD_G, LD_B$).
2. Obtain a second image using a filter with peak transmittance at 680 nm and a bandwidth of 20 nm, for example. This is a longer wavelength than the red band of the triple bandpass filter. At 680 nm, the only pigment with a significant absorption is melanin. Again extract the grayscale image (from the red channel), and convert to logs, $LD_{R'}$.
3. Use image analysis software to align the $LD_{R'}$ image with the $LD_R$, $LD_G$ and $LD_B$ images.
4. Obtain the macular pigment optical density distribution by combining the 4 images in a linear fashion—

$$D = -0.525 * LD_B + 0.355 * LD_G - 0.882 * LD_R + 2.60 * LD_{R'}$$

The numerical factors are different combinations of extinction coefficients of the 4 pigments at the 4 wavelengths, similar to those shown symbolically (4) of the specification.

Since there are four different images and four unknown pigment distributions, the cone and rod distributions can also be determined using the following equations:

$$D_{cone} = -0.391 * LD_R + 0.654 * LD_{R'}$$

$$D_{rod} = 0.0254 * LD_B = -0.355 LD_G + 1.081 LD_R - 0.826 * LD_{R'}$$

The invention claimed is:

1. Apparatus for use in measuring the density and spatial distribution of macular pigment in an eye, the apparatus comprising a camera for capturing one or more colour images of the retina of an eye under examination, one or more filters for filtering the light reaching the camera so as to provide four retinal image components the spectra of which have peaks substantially at 460 nm (blue), 530 nm (green), 600 nm (red) and 680 nm (far red) respectively, the apparatus including an image processor for processing the image or images captured by the camera, wherein the image processor is operable to perform a linear mathematical combination of logarithms of the four components, with weighting, in order to eliminate contributions from non-uniform distributions of melanin, rod photo pigments and cone photo pigments over the retina, wherein the logarithms are combined to obtain the macular pigment density D at a given location in the image by the formula:

$$D = -0.525 * LD_B + 0.355 * LD_G - 0.882 * LD_R + 2.60 * LD_{R'}$$

where $LD_B$, $LD_G$, $LD_R$ and $LD_{R'}$ are the logarithms of the differences between the intensities at a given location and a peripheral location in the blue, green, red and far red component respectively.

2. Apparatus according to claim 1, in which said one or more filters include a triple bandpass filter having a transmission spectrum which has three peaks and which is substantially zero between said peaks.

3. Apparatus according to claim 2, in which said transmission spectrum does not exceed 0.001% between said peaks.

4. Apparatus according to claim 2, in which each peak is no more than 40 nm wide.

5. Apparatus according to claim 2, in which said triple bandpass filter is situated in front of an illuminating light source, so that the spectrum of light which illuminates an eye under examination has said peaks.

6. Apparatus according to claim 2, in which one of said transmission spectrum peaks is at a wavelength of 460 mn, a second of said peaks is at 600 nm and a third of said peaks is at 530 nm.

7. Apparatus for use in the measuring of the density and spatial distribution of macular pigment in an eye under examination, the apparatus comprising an illumination device for illuminating said eye and a camera for capturing a colour image of the eye, when so illuminated, wherein the illumination device is operable to illuminate the eye with light the spectrum or combined spectrum of which has peaks substantially at 460 nm (blue), 530 nm (green), 600 nm (red) and 680 nm (far red) respectively, the apparatus including an image processor for processing the image or images captured by the camera, wherein the image processor is operable to perform a linear mathematical combination of the logarithms of the four components of the image or images, each component corresponding to one of said peaks, with weighting factors, in order to eliminate contributions from non-uniform distributions of melanin, rod photo pigments and cone photo pigments over the retina, wherein the logarithms are combined to obtain the macular pigment density D at a given location in the images by the formula:

$$D=-0.525*LD_B+0.355*LD_G-0.882*LD_R+2.60*LD_{R'}$$

where $LD_B$, $LD_G$, $LD_R$ and $LD_{R'}$ are the logarithms of the differences between the intensities at a given location and a peripheral location in the blue, green, red and far red component respectively.

8. Apparatus according to claim 7, in which the spectrum of said illuminating light falls to substantially zero between said peaks.

9. Apparatus according to claim 7, in which the illuminating device comprises a light source and a triple bandpass filter having three of said peaks in its transmission spectrum.

10. Apparatus according to claim 7, in which the processor is operable to generate an output signal in which the results of the calculation of D are represented as a macular pigment map.

11. A method of measuring macular pigment density and spatial distribution in an eye, the method comprising the steps of,
   a) capturing a colour image of the retina of the eye, the image having a first and second colour component, the first colour component having a spectrum with a first peak of which is at a wavelength at which the absorption by macular pigment is at a maximum, the second component having a second peak at which substantially no such absorption occurs and a third colour component having a spectrum which has a third peak;
   b) mathematically combining the image components at each region of the image, to remove at least some colour contributions not arising from the macular pigment and
   c) providing an output representative of the contribution of the macular pigment to the image, wherein,
   a further colour component of the retina is obtained, said further component having a peak at a different wavelength of light, and data on the further component is used in said mathematical combination to eliminate the effect of non uniform distribution of rod photopigment across the retina,
   the peaks of the spectra of the components are substantially at 460 nm (blue), 530 nm (green) 600 nm red and 680 (far red) respectively, and
   the logarithms are combined to obtain the macular pigment density, D, at a given location by the formula:

$$D=-0.525*LD_B+0.355*LD_G-0.882*LD_R+2.60*LD_{R'}$$

where $LD_B$, $LD_G$, $LD_R$ and $LD_{R'}$ are the logarithms of the differences between the intensities at the given location and a peripheral location in the blue, green, red and far red component respectively.

12. A method according to claim 11, in which the step of capturing the image involves illuminating the eye with light, the spectrum of which has said first and second peaks.

13. A method according to claim 11, in which the image is captured by means of a camera and a filter which has a first and second peak its transmission spectrum, corresponding to the first and second peaks, and which filters the light forming the image captured by the camera.

14. A method according to claim 13, in which the filter is situated in the path of light from a source of illumination to the eye.

15. A method according to claim 11, in which the further colour component is obtained by capturing a further image of the retina.

* * * * *